US012011128B2

(12) United States Patent
Hwang

(10) Patent No.: US 12,011,128 B2
(45) Date of Patent: Jun. 18, 2024

(54) STERILIZER FOR AUTONOMOUS ROBOTIC CLEANER

(71) Applicant: EISENMAN INTERNATIONAL COMPANY, Tainan (TW)

(72) Inventor: Jeng-Yang Hwang, Tainan (TW)

(73) Assignee: Eisenman International Company, Tainan (TW)

(*) Notice: Subject to any disclaimer, the term of this patent is extended or adjusted under 35 U.S.C. 154(b) by 384 days.

(21) Appl. No.: 17/412,587

(22) Filed: Aug. 26, 2021

(65) Prior Publication Data

US 2023/0066903 A1   Mar. 2, 2023

(51) Int. Cl.
A47L 11/40 (2006.01)
A47L 11/24 (2006.01)

(52) U.S. Cl.
CPC .......... *A47L 11/405* (2013.01); *A47L 11/24* (2013.01); *A47L 11/4011* (2013.01); *A47L 2201/06* (2013.01)

(58) Field of Classification Search
None
See application file for complete search history.

(56) References Cited

U.S. PATENT DOCUMENTS

2005/0010331 A1*  1/2005  Taylor ............... G05D 1/0219
                                                     318/568.12
2018/0264154 A1*  9/2018  Bettles ...................... A61L 2/10

FOREIGN PATENT DOCUMENTS

| CN | 111449577 B | | 5/2021 |
| KR | 20190021766 A | * | 3/2019 |
| TW | I583339 B | | 5/2017 |
| TW | I691303 B | | 4/2020 |
| WO | WO-2004084727 A1 | * | 10/2004 ....... A61B 5/150022 |

* cited by examiner

*Primary Examiner* — Andrew Smyth
(74) *Attorney, Agent, or Firm* — Rosenberg, Klein & Lee

(57) ABSTRACT

A sterilizer for an autonomous robotic cleaner is revealed. An ultraviolet (UV) sterilizer is disposed on a top surface of an autonomous robotic cleaner. When the autonomous robotic cleaner is moved for cleaning the floor, consumers can activate the UV sterilizer by remote control to perform sterilization of indoor environments according to their needs. Thus a clean and hygienic environment is achieved. A person or pet in area to be cleaned is detected in a real time manner by a thermal sensor module so that the UV sterilizer is turned off immediately to protect the person or pet from injuries caused by exposure to UV light.

10 Claims, 3 Drawing Sheets

STERILIZER FOR AUTONOMOUS ROBOTIC CLEANER

BACKGROUND OF THE INVENTION

Field of the Invention

The present invention relates to a sterilizer for an autonomous robotic cleaner, especially to an ultraviolet (UV) sterilizer attached to and moved along with an autonomous robotic cleaner for sterilization of indoor environments by UV light.

Description of Related Art

An autonomous robotic cleaner can move around in indoor areas to pick up dirt and dust for cleaning. Along with the progress of technology and development and design of the people in the business, the autonomous robotic cleaner available now not only have functions of automatic movement and cleaning, but also functions of obstacle detection and avoidance, level difference detection, and automatic return to base station. Some types even provide automatic detection of the charge condition for self-charging, plan of the cleaning route, and various cleaning modes in order to complete the cleaning without any assistance of users.

Refer to Taiwanese Pat. No. TW I691303(B), a self-propelled electric floor-sweeping robot is revealed. A DC motor thereof promotes the rotation speed of a side brush or enlarges the power ratio of the DC motor in execution of a wall side sweeping mode of the self-propelled electric floor-sweeping robot moving along the side wall.

Refer to Taiwanese Pat. No. TW I583339(B), a sweeping robot is disclosed. The sweeping robot is design to include a mother machine and a slave machine. The slave machine is communicating with the mother machine and detachably mounted on the mother machine. The slave machine is separated from the mother machine and capable of cleaning separately. When the mother machine is unable to enter the cleaning space, the slave machine can be separated from the mother machine to carry out cleaning duties which are unable to be performed by the mother machine.

Refer to Chinese Pat. No. CN 111449577(B), a stair-climbing cleaning robot and a working method thereof are revealed. The cleaning robot can climb stairs automatically and carry out cleaning duties while climbing stairs. Thus the cleaning robot works in a more intelligent and more efficient way.

Thus there is room for improvement and there is a need to provide a novel autonomous robotic cleaner which is not only used for cleaning the floors in order to meet users' needs.

SUMMARY OF THE INVENTION

Therefore, it is a primary object of the present invention to provide a sterilizer for an autonomous robotic cleaner in which an ultraviolet (UV) sterilizer is disposed on a main body of an autonomous robotic cleaner and moved along the moving autonomous robotic cleaner in indoor spaces for sterilization of objects in the indoor space.

In order to achieve the above object, a sterilizer for an autonomous robotic cleaner according to the present invention includes an ultraviolet (UV) sterilizer arranged at a top surface of a main body of an autonomous robotic cleaner. The UV sterilizer consists of a suction mount, a control module, a power supply module, an ultraviolet (UV) generator, and a thermal sensor module. The suction mount is fixed on the top surface of the main body of the autonomous robotic cleaner while the control module, the power supply module, the UV generator, and the thermal sensor module are all arranged at the suction mount. The control module is electrically connected to the power supply module, the UV generator, and the thermal sensor module while the power supply module provides power to the control module, the UV generator, and the thermal sensor module. The control module is operated to drive the UV generator to produce UV light for sterilization. When the UV generator emits UV light, the thermal sensor module detects whether there is a person or animal in a space to be cleaned and sends messages related to detection results to the control module. Then the control module checks whether there is a person or animal in the space to be cleaned according to the messages received. If the check result is yes, the UV generator is turned off.

The UV sterilizer further includes a wireless network communication module which is electrically connected to the control module and the power supply module. The wireless network communication module receives signals from an intelligent electronic device (IED) with network connection capabilities and then sends the signals to the control module.

The present invention has the following advantages.
1. When the autonomous robotic cleaner is moved for sweeping and cleaning the floor, users can activate the UV sterilizer to sterilize indoor environments by remote control according to their needs. Thereby the indoor environments are clean and hygienic.
2. A person or pet in the area to be cleaned is detected by a thermal sensor in a real time manner. Thus the UV sterilizer is turned off immediately, without emitting UV light which causes injuries to the person or the pet.

BRIEF DESCRIPTION OF THE DRAWINGS

The structure and the technical means adopted by the present invention to achieve the above and other objects can be best understood by referring to the following detailed description of the preferred embodiments and the accompanying drawings, wherein.

DETAILED DESCRIPTION OF THE PREFERRED EMBODIMENT

Figure 1:
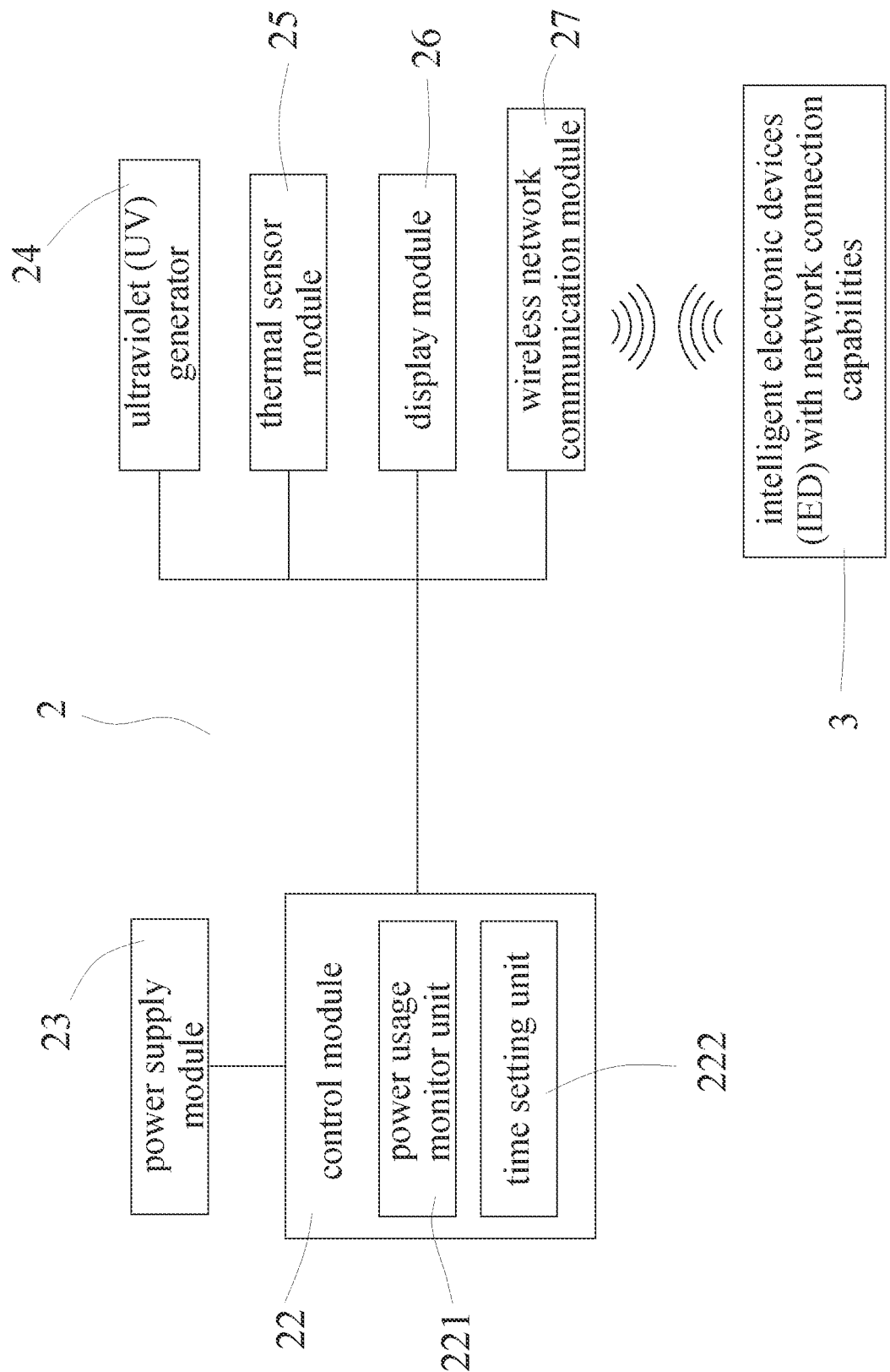
FIG. 1 is a block diagram showing circuit structure of an ultraviolet (UV) sterilizer for an autonomous robotic cleaner of an embodiment according to the present invention.
Figure 2:
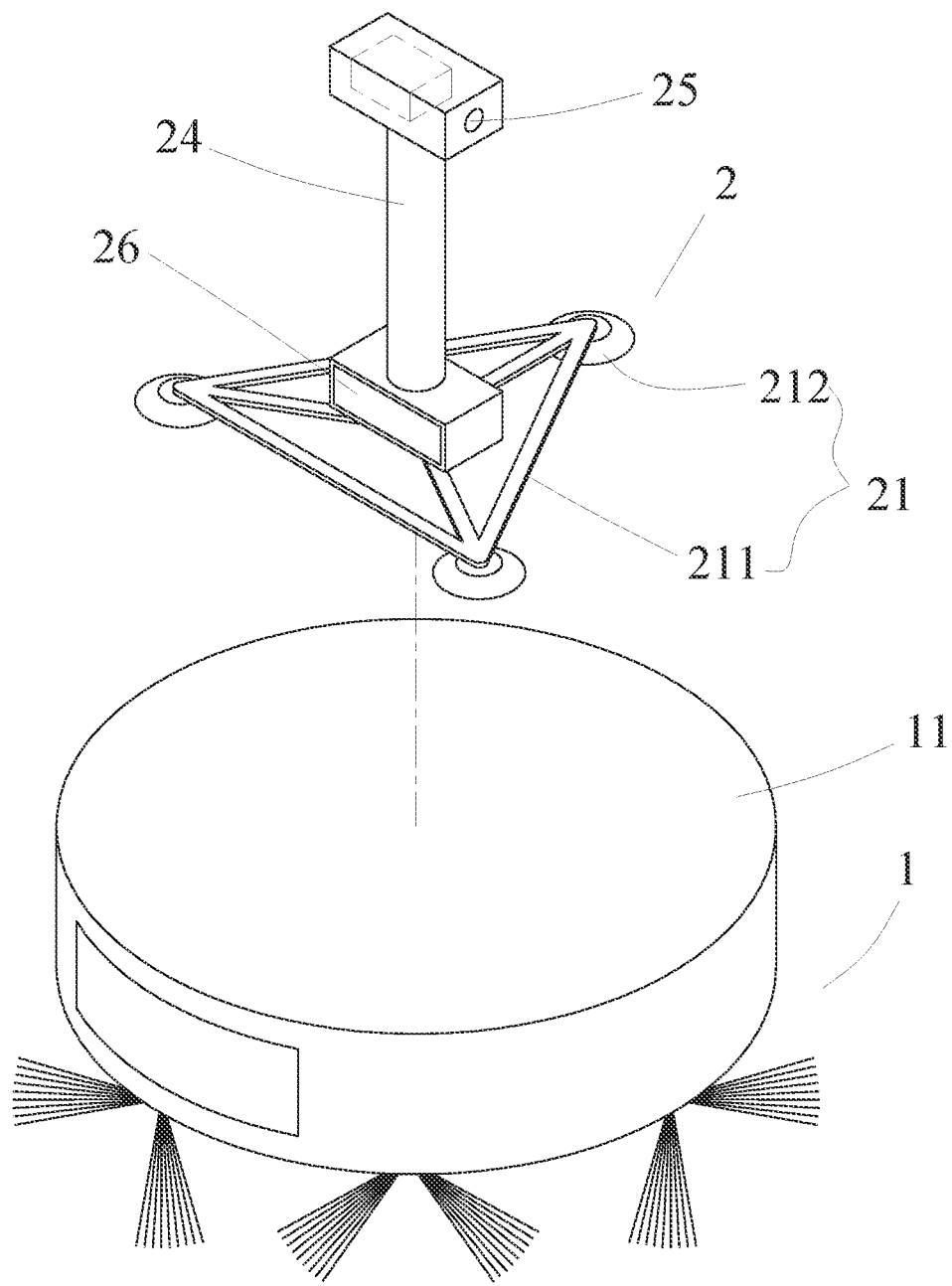
FIG. 2 is a schematic drawing showing an explosive view of an UV sterilizer and an autonomous robotic cleaner of an embodiment according to the present invention.
Figure 3:
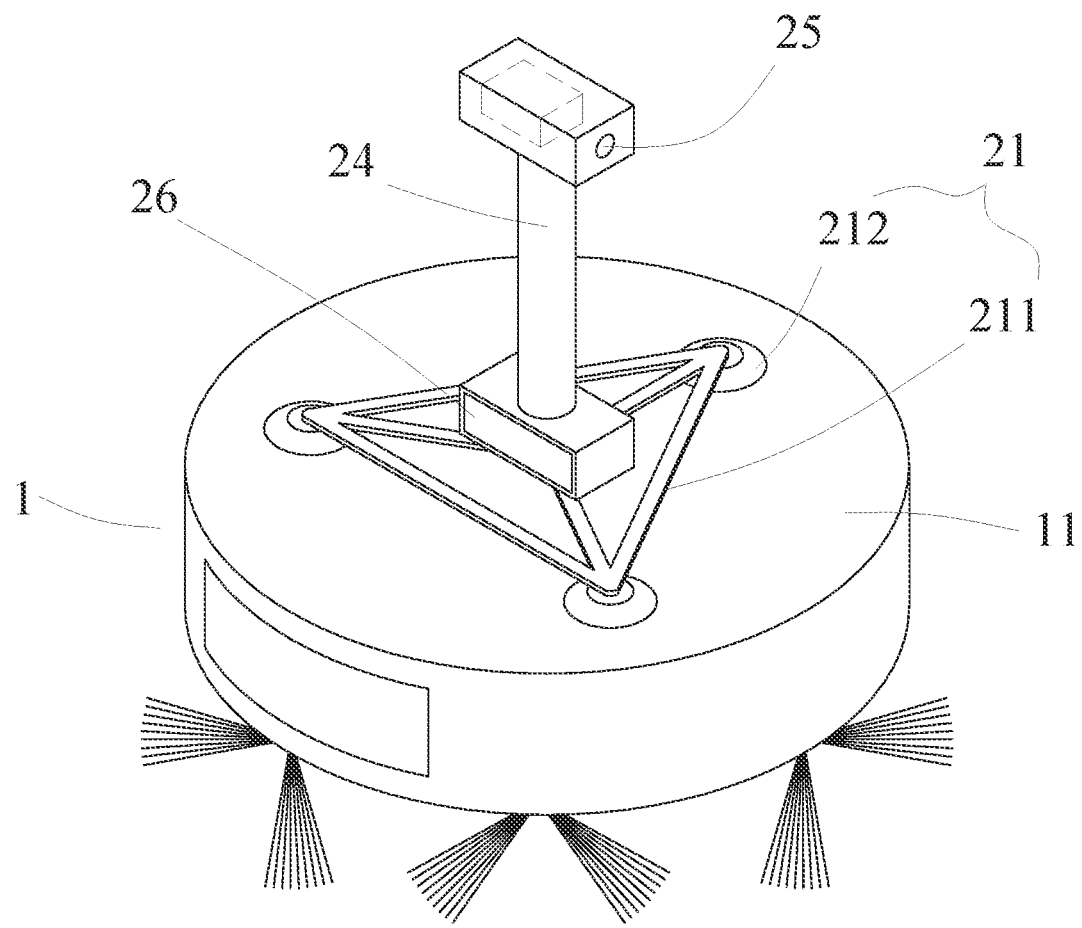
FIG. 3 is a schematic drawing showing a perspective view an UV sterilizer assembled with an autonomous robotic cleaner of an embodiment according to the present invention.

Refer to FIG. 1, FIG. 2 and FIG. 3, a sterilizer for an autonomous robotic cleaner according to the present invention is an ultraviolet (UV) sterilizer 2 disposed on a top surface 11 of a main body of an autonomous robotic cleaner 1. The UV sterilizer 2 is composed of a suction mount 21, a control module 22, a power supply module 23, an ultraviolet (UV) generator 24, and a thermal sensor module 25.

The suction mount 21 consists of a mount 211 and at least one suction cup 212. In the embodiment shown in FIG. 2 and FIG. 3, three suction cups 212 are arranged at the bottom of the mount 211 so that the mount 211 is mounted and fixed on the top surface 11 of the main body of the autonomous robotic cleaner 1 by the suction cups 212 attached to the top surface 11 of the main body. The control module 22, the power supply module 23, the UV generator 24, and the thermal sensor module 25 are all disposed on the suction mount 21.

The control module 22 is electrically connected to the power supply module 23, the UV generator 24, and the thermal sensor module 25 while the power supply module 23 supplies power to the control module 22, the UV generator 24, and the thermal sensor module 25. The control module 22 is operated to drive the UV generator 24 to produce UV light for sterilization of indoor spaces.

The thermal sensor module 25 is used for detecting whether there is a person or animal in a space to be cleaned and sending messages related to detection results to the control module 22. Under the condition that the UV generator 24 emits UV light for sterilization and disinfection, the control module 22 checks whether there is a person or animal in the space to be cleaned according to the messages from the thermal sensor module 25. When the control module 22 checks that there is no person or animal in the space to be cleaned, the UV generator 24 keeps current state under control of the control module 22. Once the control module 22 checks that there is a person or animal in the space to be cleaned, the control module 22 controls the UV generator 24 to stop working.

In a preferred embodiment, the UV sterilizer 2 further includes a display module 26 which is electrically connected to the control module 22 and the power supply module 23. The power supply module 23 provides power to the display module 26 while the control module 22 includes a power usage monitor unit 221 which is used for detecting power usage of the power supply module 23 and sending detected values of the power usage to the display module 26 to be displayed.

In a preferred embodiment, the control module 22 further includes a time setting unit 222 which is used to set on and off time of the UV generator 24 and the set on and off time of the UV generator 24 is shown on the display module 26. Users can set on and off time of the UV generator 24 by the control module 22 and the time being set is displayed on the display module 26. For example, the user can set the time the UV generator 24 will be activated and inactivated such as one day in each month, one day in each week, or a moment in each day. When the time being set is coming and the control module 22 checks that there is no person or animal in the space to be cleaned according to detection results from the thermal sensor module 25, the control module 22 of the UV sterilizer 2 activates the UV generator 24 to emit UV light for disinfection and sterilization of the space to be cleaned.

In a preferred embodiment, the UV sterilizer 2 further includes a wireless network communication module 27 which is fixed on the suction mount 21 and electrically connected to the control module 22 and the power supply module 23. The power supply module 23 supplies power to the wireless network communication module 27 which receives signals from an intelligent electronic device (IED) 3 with network connection capabilities and sends the signals to the control module 22. Thus users can remotely control the UV sterilizer 2 to turn on or turn off the UV generator 24 for UV sterilization by operating and executing a software program of the TED 3. It should be noted that the UV generator 24 only starts to emit UV light for sterilization when the thermal sensor module 25 sends detection results to the control module 22 and the control module 22 checks that there is no person in the space to be cleaned according to the detection results received. The intelligent electronic device (IED) 3 with network connection capabilities can be a wireless communication device such as a mobile phone, a tablet, a computer, etc.

Once receiving a signal for activating the UV generator 24 from the intelligent electronic device (IED) 3 with network connection capabilities, the wireless network communication module 27 sends the signal to the control module 22 and the UV generator 24 produces UV light for sterilization after the control module 22 checking that there is no person in the space to be cleaned according to the signal received.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalent.

What is claimed is:

1. An ultraviolet (UV) sterilizer for coupling to autonomous robotic cleaners, comprising:
   a suction mount configured for removable coupling on a top surface of a main body of an autonomous robotic cleaner;
   an ultraviolet (UV) generator coupled to the suction mount and thereby being removably mounted on the top surface of the main body of the autonomous robotic cleaner;
   a control module;
   a power supply module; and
   a thermal sensor module;
   wherein the UV generator extends vertically in a direction away from both the top surface of the autonomous robotic cleaner and the suction mount to thereby radiate ultraviolet (UV) radiation omnidirectionally to a surrounding environment of a space; and
   wherein the control module is electrically connected to the power supply module, the UV generator, and the thermal sensor module; wherein the power supply module supplies power to the control module, the UV generator, and the thermal sensor module; wherein the control module drives the UV generator to radiate the UV light for sterilization; wherein prior to the UV generator being turned ON for radiating the UV light, the thermal sensor module is configured to detect whether there is a person or an animal in the space to be radiated with the UV light, and the thermal sensor module is configured to send the detection results to the control module; and the control module determines whether to radiate the UV light according to the detection results sent by the thermal sensor module; wherein if the control module determines that a person or an animal is in the space to be radiated with the UV light, the control module is configured to not turn ON the UV generator and let the UV generator remain turned OFF, and the control module monitoring subsequent detection results from the thermal sensor module and turning OFF the UV generator responsive to determining that a person or an animal is in the space to be radiated with the UV light.

2. The ultraviolet (UV) sterilizer for coupling to autonomous robotic cleaners as claimed in claim 1, wherein the suction mount includes a mount and at least one suction cup arranged at a bottom of the mount for being removably attached to the top surface of the main body of the autonomous robotic cleaner.

3. The ultraviolet (UV) sterilizer for coupling to autonomous robotic cleaners as claimed in claim 2, wherein the UV sterilizer further includes a display module electrically connected to the control module and the power supply module; the power supply module supplies power to the display module, and the control module includes a power usage monitor unit for detecting power usage of the power supply module and sending detected values of the power usage of the power supply module to the display module to be displayed.

4. The ultraviolet (UV) sterilizer for coupling to autonomous robotic cleaners as claimed in claim 3, wherein the control module further includes a time setting unit, wherein ON and OFF time of the UV generator is set by the time setting unit and the set ON and OFF time of the UV generator is displayed on the display module.

5. The ultraviolet (UV) sterilizer for coupling to autonomous robotic cleaners as claimed in claim 4, wherein the UV sterilizer further includes a wireless network communication module electrically connected to the control module and the power supply module; wherein the power supply module supplies power to the wireless network communication module, the wireless network communication module receiving signals from an intelligent electronic device (IED) having network connection capabilities and sends the signals to the control module; the control module determining whether to turn ON the UV generator according to the signals received.

6. The ultraviolet (UV) sterilizer for coupling to autonomous robotic cleaners as claimed in claim 5, wherein the intelligent electronic device (IED) having network connection capabilities includes a software program stored on a non-transitory computer readable medium, the software program being executed for remotely controlling ON and OFF and the time-setting of the UV generator.

7. The ultraviolet (UV) sterilizer for coupling to autonomous robotic cleaners as claimed in claim 1, wherein the UV sterilizer further includes a display module electrically connected to the control module and the power supply module; the power supply module supplies power to the display module, and the control module includes a power usage monitor unit for detecting power usage of the power supply module and sending detected values of the power usage of the power supply module to the display module to be displayed.

8. The ultraviolet (UV) sterilizer for coupling to autonomous robotic cleaners as claimed in claim 7, wherein the control module further includes a time setting unit, wherein ON and OFF time of the UV generator is set by the time setting unit and the set ON and OFF time of the UV generator is displayed on the display module.

9. The ultraviolet (UV) sterilizer for coupling to autonomous robotic cleaners as claimed in claim 8, wherein the UV sterilizer further includes a wireless network communication module electrically connected to the control module and the power supply module; wherein the power supply module supplies power to the wireless network communication module, the wireless network communication module receiving signals from an intelligent electronic device (IED) having network connection capabilities and sends the signals to the control module; the control module determining whether to turn ON the UV generator according to the signals received.

10. The ultraviolet (UV) sterilizer for coupling to autonomous robotic cleaners as claimed in claim 9, wherein the intelligent electronic device (IED) having network connection capabilities includes a non-transitory software program stored on a non-transitory computer readable medium, the software program being executed for remotely controlling ON and OFF and the time-setting of the UV generator.

\* \* \* \* \*